United States Patent [19]

Douglas, Jr.

[11] Patent Number: 4,892,483

[45] Date of Patent: Jan. 9, 1990

[54] ORAL DRUG RETAINING DEVICE

[75] Inventor: Jesse B. Douglas, Jr., Lexington, Ky.

[73] Assignee: The University of Kentucky Research Foundation, Lexington, Ky.

[21] Appl. No.: 231,959

[22] Filed: Aug. 15, 1988

[51] Int. Cl.$^4$ ................................................ A61C 5/00
[52] U.S. Cl. ...................................... 433/229; 433/80; 433/215
[58] Field of Search ........................... 433/215, 229, 80

[56] References Cited

U.S. PATENT DOCUMENTS 3,600,807  8/1971  Sipos .................................... 433/229

Primary Examiner—Robert Peshock
Attorney, Agent, or Firm—King and Schickli

[57] ABSTRACT

An oral drug retaining device includes a receptacle for receiving and holding a polymer matrix impregnated with a pharmacologic agent. The receptacle is formed by a cooperating basket and frame. The basket and frame include a hinge at one side and a latch pin at the opposite side to allow the receptacle to be selectively opened and closed to replace the polymer matrix as desired. Cooperating male and female connectors are provided to allow the receptacle to be releasably mounted to a tooth of a patient. One of these connectors is adapted for mounting to a tooth while the other is attached to the frame of the receptacle.

3 Claims, 1 Drawing Sheet

ORAL DRUG RETAINING DEVICE

TECHNICAL FIELD

The present invention relates generally to a device particularly adapted for retaining a pharmacologic agent or agents for release in the oral cavity of a patient.

BACKGROUND OF THE INVENTION

It has long been recognized that the application of fluorides and antibacterial agents to the teeth and gums serves to prevent tooth decay and the onset of periodontal disease. The utilization of fluorides and antibacterial agents in toothpaste, mouth washes and rinses only meets with limited success, however, largely due to the low retention time of these agents in the oral cavity after application.

A number of devices have been developed in the art to address this problem and provide retention of the fluorides and antibacterial agents in the oral cavity so as to enhance their beneficial effects. U.S. Pat. No. 4,175,326 to Goodson discloses a device for localized oral treatment and/or diagnosis. The Goodson device includes capillary fibers which are laced around the teeth and the ends tied together. Unfortunately, such a device is generally only suited for a single localized application. It is not refillable and must be physically removed and a fresh device reinstalled for additional applications. Such a procedure is inconvenient, requiring a substantial amount of time while also serving to increase the overall cost of treatment. Additionally, no protection is provided for the fibers against physical damage from sources such as toothbrushing and mastication. As such, utilization of the device is generally limited to fluoride, antibacterial agents and other dental treatment applications.

U.S. Pat. No. 4,681,544 to Anthony discloses a device for positioning and retaining an oral pack for protecting a surgical site. The pack may be fabricated of a polymeric material for localized medication delivery. The use of this device is for a temporary application at best. This device does not address the problem of protecting the polymeric material from physical damage. Additionally, the device is attached to the tooth by the use of a monofilament cord looped and tied around the tooth, increasing difficulty in placement and attachment.

A need exists, therefore, for an improved oral drug retaining device for administration of pharmacologic agents within the oral cavity. Such a device should be simple to install and provide protection from physical damage. As such, unlike the prior art devices discussed above, this device would not be limited to administering medication for dental applications. Instead, the device would also be adapted for retaining drugs or pharmacologic agents, utilized in treating a wide range of afflictions throughout the body, for absorption directly through the oral mucosal epithelium. It would also be utilized to allow certain drugs or agents to be systemically released via ingestion through the gastrointestinal tract in a slow, daily, continuous time released fashion.

SUMMARY OF THE INVENTION

Accordingly, it is a primary object of the present invention to provide an improved oral drug retaining device overcoming the limitations and disadvantages of the prior art.

Another object of the present invention is to provide an oral drug retaining device facilitating a localized and/or time released application of pharmacologic agent(s).

An additional object of the present invention is to provide an oral drug retaining device allowing certain drugs which are incompatible with the stomach to be absorbed into the body directly through the oral mucosal epithelium.

An additional object of the present invention is to provide an oral drug retaining device which is simple and easy to install and provides for easy drug replenishment through the use of a readily replaceable drug impregnated polymer matrix.

Still another object of the present invention is to provide an oral drug retaining device providing substantially complete protection of a drug impregnated polymer from physical damage.

Yet another object of the present invention is to provide an oral drug retaining device having a receptacle for retaining a polymer matrix, which may be simply and completely removed from the mouth and repositioned later, allowing periodic drug administration at the convenience and control of the patient.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an oral drug retaining device is provided to direct the application of a pharmacologic agent or agents in a localized and/or time release manner. The device utilizes a polymer matrix impregnated with pharmacologic agent(s). The matrix is contained within a receptacle which is mounted to the surface of a tooth. The generally preferred location for attachment is the outer surface of the first permanent molar. This minimizes wearer discomfort while maximizing absorption potential.

In the preferred embodiment, the receptacle is a basket including relatively wide spaced bands to retain and protect the polymer matrix. The bands are fabricated of a strong, hypoallergenic material such as stainless steel, to substantially prevent physical damage to the polymer matrix by toothbrushing, mastication or the like. Advantageously, the open spaces in the basket between the bands allow free dispersal of the drug from the polymer matrix.

The basket further includes a frame and connectors for mounting to the surface of a tooth. The male and female connectors can be engaged/disengaged to install/remove the device from the mouth. A ligature wire can be utilized to further retain the device in place within the mouth. Advantageously, this configuration securely retains the device within the mouth yet provides for simple removal of the retaining device if desired as, for example, for cessation of drug application.

In the preferred embodiment, the male and female connectors cooperate in a sliding dovetail configuration. The female connector includes a bonding pad for permanent attachment by the use of cement or similar conventional orthodontic means to the surface of the tooth. The male connector is attached to the frame of the basket.

The basket is pivotably retained on the frame by a hinge. By simply pivoting the basket open, an impregnated polymer matrix may be easily placed in position for retention within the basket. The basket is then pivoted closed around the matrix and a latch pin is passed through corresponding eyes provided on the opposite side of the basket and frame to lock the matrix in place. This, of course, serves to prevent accidental release. In this manner, the basket, frame and base cooperate to securely retain and protect the matrix, yet allow easy removal from the oral cavity.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principals of the invention. In the drawing.

Reference will now be made in detail to the present preferred embodiment of the invention, an example of which is illustrated in the accompanying drawing.

DETAILED DESCRIPTION OF THE INVENTION

Figure 1:
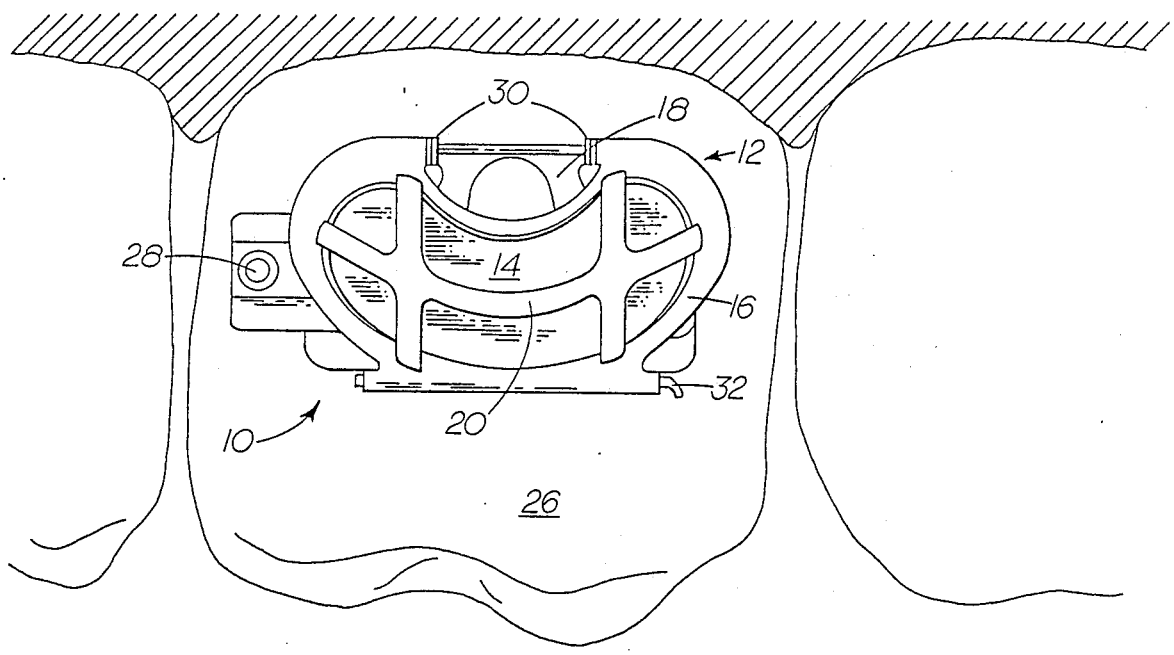
FIG. 1 is a front elevational view of the oral drug retaining device mounted upon the surface of a tooth.
Figure 2:
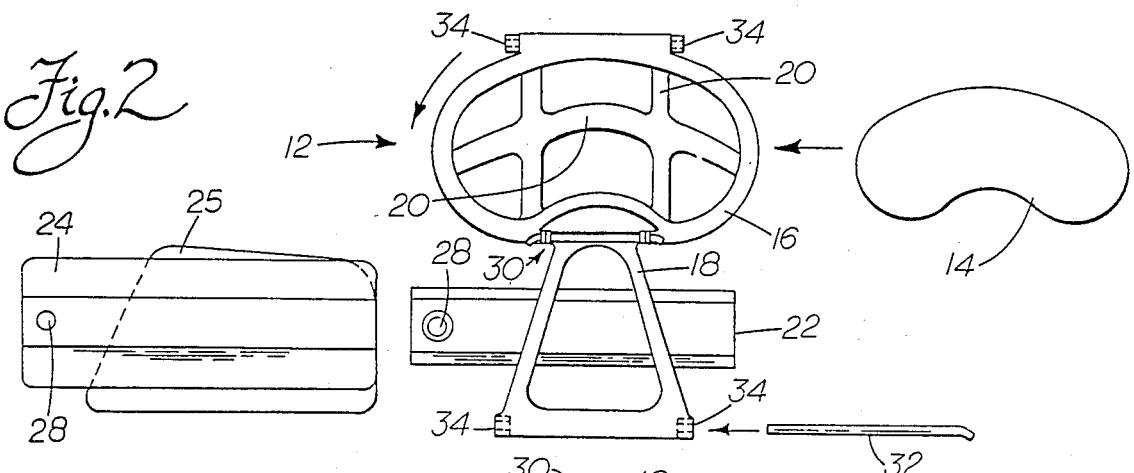
FIG. 2 is an exploded view of the oral drug retaining device illustrating the male and female connecting members, the basket retainer and the polymer matrix.

Reference is now made to FIGS. 1 and 2 showing the oral drug retaining device 10 of the present invention. The device 10 includes a receptacle 12 for retaining a polymer matrix 14 impregnated with a pharmacologic agent or agents. The use of an impregnated polymer matrix for dispensing pharmacologic agents is well known in the art. The matrix 14 may be provided to supply a localized application of any appropriate pharmacologic agent or drug, such as fluoride to the teeth and gums of a patient. Because the fluoride is continuously released over time, treatment time is increased over simple toothpaste, mouth wash and rinse applications and as such, the beneficial results are enhanced.

Advantageously, the present invention may also be utilized to allow other drugs, such as pain relievers, adrenergics, etc., to be absorbed over time directly through the oral mucosal epithelium. In this manner, certain drugs which are incompatible with the stomach can be safely administered through the mouth. As a result, a patient need not resort to painful injections in order to receive treatment.

As shown in FIG. 2, the receptacle 12 includes a basket 16 connected to a mounting frame 18. The basket 16 is fabricated from a series of bands 20. Each band 20 as well as the frame 18 is formed of a hypoallergenic material such as stainless steel. Use of such a material provides sufficient strength to withstand physical damage due to toothbrushing and mastication. At the same time the receptacle 12 can be used in substantially all patient applications with only a small probability of allergic rejection. Advantageously, the use of a strong material like stainless steel also allows the provision of relatively large, open spaces or areas in between the bands 20 of the basket 16 without sacrificing structural rigidity. This provides for substantially unrestricted dispersion of the drug contained within the polymer matrix 14 into the oral cavity.

Figure 3:
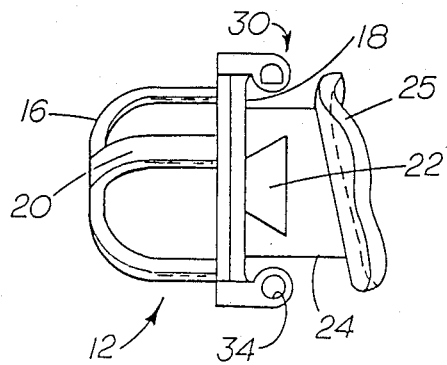
FIG. 3 is a side elevational view of the oral drug retaining device illustrating the male and female dovetail connection and the bonding pad which attaches directly to the surface of a tooth.

As shown in FIGS. 1-3, the receptacle 12 is mounted or secured to a tooth, such as the first permanent upper molar by two interconnecting members; male connector 22 attached to the mounting frame 18 and a female connector 24. The tooth side of the female connector 24 includes a bonding pad 25 (see FIG. 3) for attachment to the surface of a tooth 26. This attachment can be made by cement or similar conventional orthodontic means.

Once the female connector 24 is mounted onto the surface of the tooth, installation of the receptacle 12 involves simply sliding the male connector 22 into dovetail engagement with the female connector 24. This provides a secure strong engagement of the connectors 22, 24.

Where desired, a ligation wire (not shown) may also be used to tie the connectors 22 and 24 together once installed, further securely retaining the device 10 within the mouth. The ligation wire is passed through aligned ligating eyes 28 in the connectors 22 and 24 and then tied. Removal of the device 10 is simply a reversal of the above procedure. In this manner, the device 10 may be simply installed or removed as desired by the physician, dentist or even the patient.

Advantageously, installation and/or replacement of the polymer matrix 14 within the receptacle 12 is facilitated by the pivotal connection provided between the basket 16 and the frame 18. In the preferred embodiment, this pivotal connection is a hinge 30 (see FIGS. 2 and 3). Initial installation of the matrix 14 is performed by pivoting the basket 16 upwardly away from the frame 18, placing the matrix within the basket and rotating the basket downwardly to again meet the frame. A latch pin 32 is then passed through aligned eyes 34 on the basket 16 and frame 18 to securely lock the basket in the closed position.

After a certain period of time, substantially all of the pharmacologic agent is leached from the polymer matrix 14. Thus, if treatment is to continue, the matrix 14 must be replaced. This is easily accomplished with the present device 10. More specifically, the latch pin 32 is removed and the basket 16 pivoted open. The old matrix 14 is removed and replaced with a new one. The basket 16 is then again pivoted closed and the latch pin 32 reinserted through the eyelets 34. Thus, the patient may conveniently replace the matrix 14 in order to continue treatment as desired without the assistance of a nurse, dentist, physician, or technician.

In summary, numerous benefits result from employing the concepts of the present invention. The oral drug retaining device 10 provides for localized or time release dosage of medication within the oral cavity. The device 10 includes a retainer 12 containing a polymer matrix 14 impregnated with a pharmacologic agent. The retainer 12 protects the matrix 14 from physical damage. The device 10 is adapted for simple and reliable installation/removal in the mouth for replacement of the polymer or cessation of drug application as required.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. An apparatus for retaining a matrix impregnated with a pharmacologic agent in the mouth of a patient, comprising:
   receptacle means including a basket and a frame for receiving and protecting said impregnated matrix from physical damage due to mastication and tooth brushing;
   means for opening and closing said basket and said frame including latch means and hinge means on opposing sides of said basket and said frame that allow replacement of said impregnated matrix; and
   means for mounting said receptacle means to a tooth of the patient.

2. The apparatus set forth in claim 1 wherein said latch means includes a latch pin passed through corresponding eyes provided on said basket and said frame.

3. The apparatus set forth in claim 1 wherein said mounting means includes cooperating male and female connectors, one connector adapted for connection to a tooth and one connector mounted to said receptacle means.

* * * * *